(12) United States Patent
Lin et al.

(10) Patent No.: US 9,890,206 B2
(45) Date of Patent: Feb. 13, 2018

(54) H1N1 FLU VIRUS NEUTRALIZING ANTIBODIES

(71) Applicant: Medigen Biotechnology Corporation, Taipei (TW)

(72) Inventors: Young-Sun Lin, Taipei (TW); Kuei-Tai Lai, Taipei (TW); Huei-Luen Huang, Taipei (TW); Hsiang-Ting Hsu, Taipei (TW); Wan-Chen Chen, Taipei (TW); Ya-Lin Chen, Taipei (TW); Chia-Wen Wong, Taipei (TW)

(73) Assignee: Medigen Biotechnology Corporation, Taipei (TW)

( * ) Notice: Subject to any disclaimer, the term of this patent is extended or adjusted under 35 U.S.C. 154(b) by 162 days.

(21) Appl. No.: 14/831,167

(22) Filed: Aug. 20, 2015

(65) Prior Publication Data

US 2017/0051046 A1    Feb. 23, 2017

(51) Int. Cl.
*A61K 45/06* (2006.01)
*C07K 16/10* (2006.01)
*G01N 33/569* (2006.01)
*A61K 39/00* (2006.01)

(52) U.S. Cl.
CPC .... *C07K 16/1018* (2013.01); *A61K 2039/505* (2013.01); *C07K 2317/565* (2013.01); *C07K 2317/76* (2013.01); *G01N 33/56983* (2013.01); *G01N 2333/11* (2013.01)

(58) Field of Classification Search
None
See application file for complete search history.

(56) References Cited

U.S. PATENT DOCUMENTS 8,916,160 B2 * 12/2014 Grandea, III .... G01N 33/56983
424/159.1
9,527,924 B2 * 12/2016 Marasco .............. A61K 39/145

OTHER PUBLICATIONS

Krause et al. (Journal of Virology, 2011, p. 10905-10908).*

* cited by examiner

*Primary Examiner* — Agnieszka Boesen
(74) *Attorney, Agent, or Firm* — Liang Legal Group, PLLC

(57) ABSTRACT

An antibody, or a binding fragment of the antibody, against H1N1 virus, includes a heavy chain variable region and a light chain variable region, wherein the heavy chain variable region contains complementarity determining regions (CDR) that have the amino acid sequences of SEQ ID NO: 5, SEQ ID NO: 6, and SEQ ID NO: 7; and wherein the light chain variable region contains complementarity determining regions that have the amino acid sequences of SEQ ID NO: 8, SEQ ID NO: 9, and SEQ ID NO: 10. A method for treating or preventing H1N1 infection in a subject includes administering to the subject the antibody or the binding fragment of the antibody.

9 Claims, 14 Drawing Sheets

10 →

Isolating memory B Cells — 11

↓

Immortalizing memory B Cells — 12

↓

Screening for B Cells secreting antibodies binding to HA and/or inhibiting HA activity — 13

↓

Screening for B Cells secreting antibodies that can neutralize viruses — 14

FIG. 1

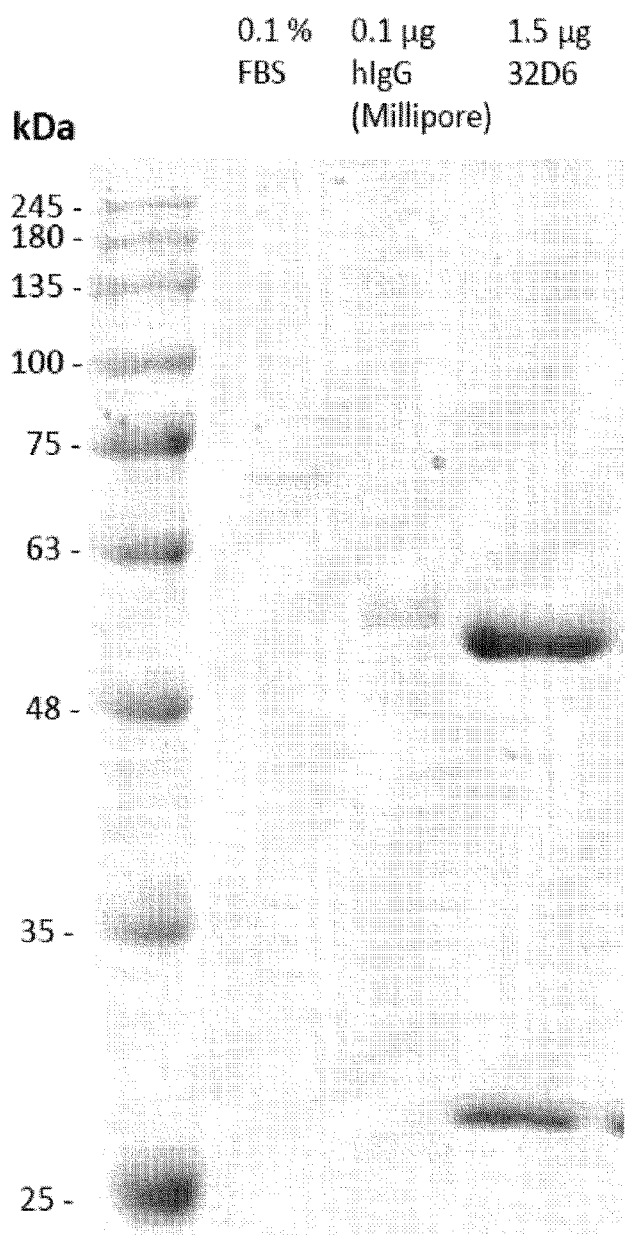 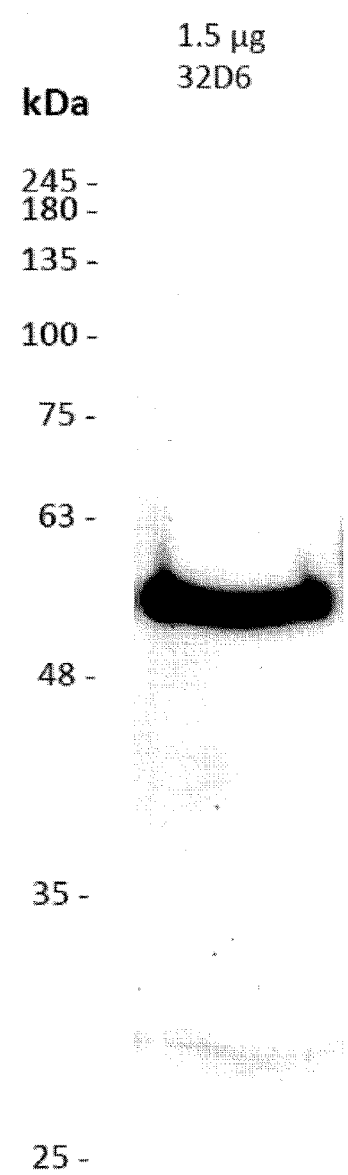
FIG. 2(A)  FIG. 2(B)

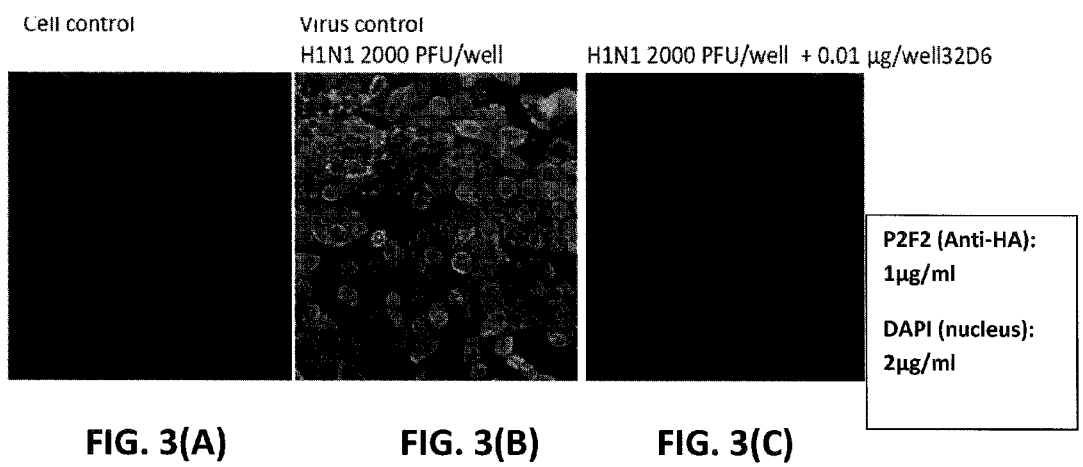
FIG. 3(A)  FIG. 3(B)  FIG. 3(C)
P2F2 (Anti-HA): 1μg/ml
DAPI (nucleus): 2μg/ml
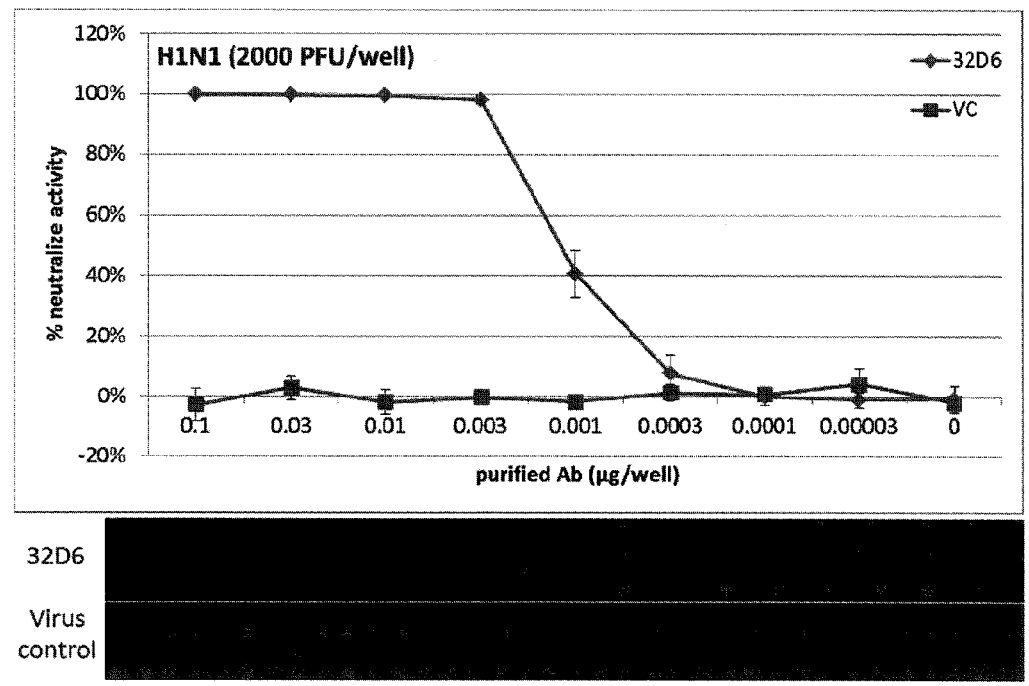
FIG. 4(A)

FIG. 4(D)

FIG. 5(A)  (32D6, Heavy Chain; SEQ ID NO: 1)

ATGAAACACCCGTGGTTCTTCCTCCTCCTGGTGGCAGCTCCCAGATGGGTCCTGTCCCAGGTGCAGCTGCAGGAGT
CGGGCCCAGGACTGGTGAAGCCTTCGGAGACCCTGTCCCTCACCTGCACTGTCTCT<u>GGTGGCTCCGTCAACACTG
GCAGTTACTACTGGAGC</u>TGGATCCGGCAGCCCCCAGGGAAGGGACTGGAGTGGATTGCG<u>TATTCCTCTGTCAGT
GGGACCTCCAAC</u>TACAATCCCTCCCTCAAGAGTCGAGTCACCCTGACAGTAGACACGTCCAAGAACCAGTTCTCCC
TGAGCGTGAGGTCTGTGACCGCTGCGGACACGGCCGTATATTTCTGTGCGAGA<u>CTAAATTACGATATTTTGACTG
GTTATTACTTCTTTGACTTC</u>TGGGGCCAGGGAACCCTGGTCATCGTCTCCTCAGCCTCCACCAAGGGCCCATCGGT
CTTCCCCCTGGCACCCTCCTCCAAGAGCGCCTCTGGGGGCACAGCGGCCCTGGGCTGCCTGGTCAAGGACTACTTC
CCCGAACCGGTGACGGTGTCGTGGAACTCAGGCGCCCTGACCAGCGGCGTGCACACCTTCCCGGCTGTCCTACAG
TCCTCAGGACTCTACTCCCTCAGCAGCGTGGTGACCGTGCCCTCCAGCAGCTCGGGCACCCAGACCTACATCTGCA
ACGTGAATCACAAGCCCAGCAACACCAAGGTGGACAAGAGAGTTGAGCCCAAATCTTGTGACAAAACTCACACAT
GCCCACCGTGCCCAGCACCTGAACTCCTGGGGGGACCGTCAGTCTTCCTCTTCCCCCCAAAACCCAAGGACACCCT
CATGATCTCCCGGACCCCTGAGGTCACATGCGTGGTGGTGGACGTGAGCCACGAAGACCCTGAGGTCAAGTTCAA
CTGGTACGTGGACGGCGTGGAGGTGCATAATGCCAAGACAAAGCCGCGGGAGGAGCAGTACAACAGCACGTACC
GTGTGGTCAGCGTCCTCACCGTCCTGCACCAGGACTGGCTGAATGGCAAGGAGTACAAGTGCAAGGTCTCCAACA
AAGCCCTCCCAGCCCCCATCGAGAAAACCATCTCCAAAGCCAAAGGGCAGCCCCGAGAACCACAGGTGTACACCC
TGCCCCCATCCCGGGATGAGCTGACCAAGAACCAGGTCAGCCTGACCTGCCTGGTCAAAGGCTTCTATCCCAGCG
ACATCGCCGTGGAGTGGGAGAGCAATGGGCAGCCGGAGAACAACTACAAGACCACGCCTCCCGTGCTGGACTCC
GACGGCTCCTTCTTCCTCTACAGCAAGCTCACCGTGGACAAGAGCAGGTGGCAGCAGGGGAACGTCTTCTCATGC
TCCGTGATGCATGAGGCTCTGCACAACCACTACACGCAGAAGAGCCTCTCCCTGTCTCCGGGTAAATGA

FIG. 5(B)  (32D6, Heavy Chain; SEQ ID NO: 2)

MKHPWFFLLLVAAPRWVLSQVQLQESGPGLVKPSETLSLTCTVS<u>GGSVNTGSYYWS</u>WIRQPPGKGLEWIA<u>YSSVSGT
SN</u>YNPSLKSRVTLTVDTSKNQFSLSVRSVTAADTAVYFCAR<u>LNYDILTGYYFFDF</u>WGQGTLVIVSSASTKGPSVFPLAPSS
KSASGGTAALGCLVKDYFPEPVTVSWNSGALTSGVHTFPAVLQSSGLYSLSSVVTVPSSSSGTQTYICNVNHKPSNTKVD
KRVEPKSCDKTHTCPPCPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGNVFSCSVMHEALHNHYTQKSLSLSPGK*

FIG. 5(C) (32D6, Light Chain; SEQ ID NO: 3)

ATGGCTTGGACCCCACTCCTCTTCCTCACCCTCCTCCTCCACTGCACAGGGTCTCTCTCCCAGGTTGAGCTGACTC
AATCGCCCTCTGCCTCTGCCTCCCTGGGAACCTCGGTCAAGCTCACCTGC<u>ACTTTGAGTAGTGGGCACAGCACCTA
CGCCATCGCG</u>TGGCATCAGCAGCGGCCAGGGAAGGGCCCCCGGTAC<u>CTGATGAATCTTAGCAGTGGA</u>GGCAGAC
ACACCAGGGGGGACGGGATCCCTGATCGCTTCTCGGGCTCCAGCTCTGGGGCTGACCGCTACCTCATCATCTCCAG
CCTCCAGTCTGAGGATGAGGCTGACTATTACTGT<u>CAGACCTGGGACGCTGGCATGGTA</u>TTCGGCGGAGGGACCA
AGCTGACCGTCCTAGGTCAGCCCAAGGCTGCCCCCTCGGTCACTCTGTTCCCGCCCTCCTCTGAGGAGCTTCAAGC
CAACAAGGCCACACTGGTGTGTCTCATAAGTGACTTCTACCCGGGAGCCGTGACAGTGGCCTGGAAGGCAGATAG
CAGCCCCGTCAAGGCGGGAGTGGAGACCACCACACCCTCCAAACAAAGCAACAACAAGTACGCGGCCAGCAGCT
ATCTGAGCCTGACGCCTGAGCAGTGGAAGTCCCACAGAAGCTACAGCTGCCAGGTCACGCATGAAGGGAGCACC
GTGGAGAAGA CAGTGGCCCCTACAGAATGTTCATAG

FIG. 5(D) (32D6, Light Chain; SEQ ID NO: 4)

MAWTPLLFLTLLLHCTGSLSQVELTQSPSASASLGTSVKLTC<u>TLSSGHSTYAIA</u>WHQQRPGKGPRY<u>LMNLSSG</u>GRHTRG
DGIPDRFSGSSSGADRYLIISSLQSEDEADYYC<u>QTWDAGMV</u>FGGGTKLTVLGQPKAAPSVTLFPPSSEELQANKATLVCL
ISDFYPGAVTVAWKADSSPVKAGVETTTPSKQSNNKYAASSYLSLTPEQWKSHRSYSCQVTHEGSTVEKTVAPTECS*

FIG. 5(E)

| CDR regions | Heavy Chain | SEQ ID NOs | Light Chain | SEQ ID NOs |
|---|---|---|---|---|
| CDR1 | GGSVNTGSYYWS | SEQ ID NO: 5 | TLSSGHSTYAIA | SEQ ID NO: 8 |
| CDR2 | YSSVSGTSN | SEQ ID NO: 6 | LMNLSSG | SEQ ID NO: 9 |
| CDR3 | LNYDILTGYYFFDF | SEQ ID NO: 7 | QTWDAGMV | SEQ ID NO: 10 |

Expression vector map of pXC-17.4

H1N1 FLU VIRUS NEUTRALIZING ANTIBODIES

BACKGROUND OF THE INVENTION

Field of the Invention

The present invention relates generally to the fields of treatment and prevention of influenza virus infections using antibodies or fragments thereof. More particularly, it relates to the development of monoclonal antibodies for use in the diagnosis, prevention and treatment of H1N1 infections.

Background

When an infection breaks out, finding an effective treatment or prevention in a timely manner is critical in order to control the spread of the disease. The urgency of finding effective treatments is highlighted by recent outbreaks, such as the H1N1 outbreak of 2009.

The 2009 H1N1 influenza outbreak inflicted more than 60 million patients and more than a quarter million required hospitalization. The 2009 H1N1 pandemic influenza virus, which is designated as A(H1N1)pdm09 by WHO, disproportionally caused severe syndromes in young children and the elderly.

The highly infectious nature of H1N1 prompted an unusually swift and intense effort to find a vaccine to prevent further spread of this illness. Due to this intense effort, an effective H1N1 vaccine, PANFLU.1, became available five months after the outbreak. This vaccine was effective in inducing immune responses in more than 90% of people aged between 12 and 60 years old. However, this vaccine was less effective in children and elderly and was ineffective in people with compromised immune system.

To have an effective counter measure during an outbreak, it is important to have passive immunotherapy to provide immediate protection. In addition, passive immunotherapy can also be used to treat infected individuals. Passive immunotherapies require antibodies that are effective in the preventing infection by the infectious agents. Such antibodies may be developed using various technologies, typically using a virus-derived antigen or an inactivated virus to induce antibodies in a suitable subject. In addition, such antibodies may be isolated from patients who had been infected by the virus and have since recovered from the illness.

For example, Hao Wang et al. (Cellular & Molecular Immunology, (2013) 10, 403-412) discloses an approach for screening viral neutralizing monoclonal antibodies (mAbs) from individuals vaccinated with the 2009 pandemic H1N1 vaccine PANFLU.1. Specifically, B cells from immunized individuals were isolated and immortalized by fusion with Epstein-Barr virus (EBV). The Epstein-Barr virus (EBV)-immortalized memory B cells were screened. From this screening, seven mAbs were identified with both high viral neutralizing capacities and hemagglutination inhibition (HAI) activities against the 2009 pandemic H1N1 viruses. These mAbs may be used for passive immunotherapy of infected patients.

While screening from memory B cells derived from donors vaccinated with a specific antigen can provide useful monoclonal antibodies against H1N1, there is still a need for better antibodies for the prevention and treatment of influenza infections (e.g., H1N1 infection).

SUMMARY OF THE INVENTION

Embodiments of the present invention relate to antibodies or binding fragments thereof against H1N1. The binding fragments of such antibodies may include Fab, scFv, F(ab')2, etc. Some embodiments of the invention relate to vectors or host cells for expressing such antibodies or fragments. Some embodiments of the invention relate to methods for preventing or treating H1N1 infection.

One aspect of the invention relates to antibodies or binding fragments thereof, against H1N1 virus. An antibody or a binding fragment thereof in accordance with one embodiment of the invention includes a heavy chain variable region and a light chain variable region, wherein the heavy chain variable region contains complementarity determining regions (CDR) that have the amino acid sequences of SEQ ID NO: 5, SEQ ID NO: 6, and SEQ ID NO: 7; and wherein the light chain variable region contains complementarity determining regions that have the amino acid sequences of SEQ ID NO: 8, SEQ ID NO: 9, and SEQ ID NO: 10.

In accordance with any of the above embodiments, the antibody may comprise a heavy chain having the amino acid sequence of SEQ ID NO: 2 and a light chain having the amino acid sequence of SEQ ID NO: 4. In accordance with any of the above embodiments, the H1N1 virus is a 2009 pandemic strain or a post 2009 strain.

Another aspect of the invention relates to expression vectors for expressing an antibody in accordance with embodiments of the invention. An expression vector in accordance with one embodiment of the invention comprises a polynucleotide sequence encoding an antibody, or a binding fragment thereof, wherein a heavy chain variable region of the antibody comprises complementarity determining regions (CDR) having the amino acid sequences of SEQ ID NO: 5, SEQ ID NO: 6, and SEQ ID NO: 7; and a light chain variable region of the antibody comprises complementarity determining regions having the amino acid sequences of SEQ ID NO: 8, SEQ ID NO: 9, and SEQ ID NO: 10.

In accordance with any of the above expression vectors, the polynucleotide sequence comprises a first polynucleotide region encoding for a heavy chain of the antibody that has the amino acid sequence of SEQ ID NO:2 and a second polynucleotide region encoding a light chain of the antibody that has the amino acid sequence of SEQ ID NO:4.

In accordance with any of the above expression vectors, the first polynucleotide region comprises the sequence of SEQ ID NO:1 and the second polynucleotide region comprises the sequence of SEQ ID NO:3.

In accordance with any of the above expression vectors, the polynucleotide sequence is linked with a glutamine synthase (GS) gene that encodes glutamine synthase.

Another aspect of the invention relates to host cells. A host cell of the invention may comprise any of the above expression vectors. The host cells may be a mammalian cell, a yeast cell, or an insect cell, such as CHO cells, *Pichia* cells, or sf9 cells.

Another aspect of the invention relates to methods for treating or preventing H1N1 infection. A method for treating or preventing H1N1 infection in accordance with one embodiment of the invention comprises administering to a subject in need of such treatments any antibody of the invention or a binding fragment thereof.

Another aspect of the invention relates to methods for detecting H1N1. A method for detecting H1N1 in accordance with embodiments of the invention comprises contacting a test sample with any of the above-described antibodies, or a binding fragment thereof; and determining presence or absence of binding with the antibody, or the binding fragment thereof, wherein presence of the binding indicates existence of H1N1 virus in the test sample.

Other aspects of the invention would be apparent to one skilled in the art in view of the drawings and the detailed description.

BRIEF DESCRIPTION OF THE DRAWINGS

FIG. 1 shows a flow chart illustrating one method for identifying an antibody from memory B cells in accordance with one embodiment of the invention.

FIG. 2(A) shows SDS PAGE and FIG. 2(B) shows a Western blot of isolated 32D6 antibody in accordance with embodiments of the invention.

FIG. 3(A) shows control cells, FIG. 3(B) shows cells infected with H1N1, and FIG. 3(C) shows the ability of 32D6 to neutralize the virus infection of the cells in accordance with embodiments of the invention.

FIG. 4(A) shows concentration dependence of the 32D6 activities in neutralizing H1N1 infection of the cells in accordance with embodiments of the invention. FIG. 4(D) shows that 32D6 cannot neutralize the infection abilities of H5N1 and H7N9 viruses.

FIG. 5(A) shows the heavy chain nucleic acid sequences with CDR sequences underlined for 32D6. FIG. 5(B) shows the heavy chain amino acid sequences with CDR sequences underlined for 32D6. FIG. 5(C) shows the light chain nucleic acid sequences with CDR sequences underlined for 32D6. FIG. 5(D) shows the light chain amino acid sequences with CDR sequences underlined for 32D6. FIG. 5(E) shows the CDR sequences for 32D6.

DEFINITION

Figure 2C:
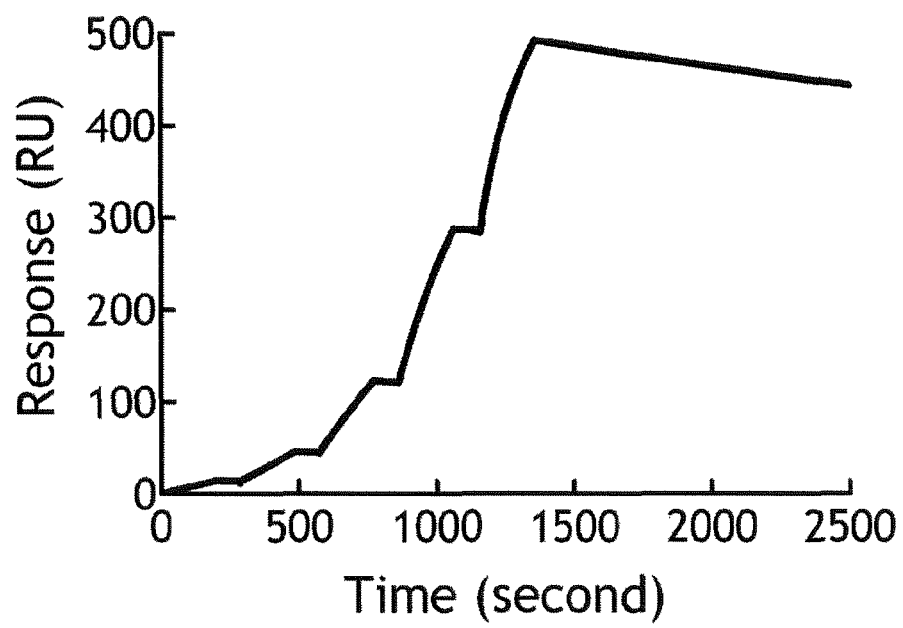
FIG. 2(C) shows the binding of 32D6 and HA using Biacore assay in accordance with embodiments of the invention.

Unless otherwise defined, scientific and technical terms used herein shall have the meanings that are commonly understood by those of ordinary skill in the art. Furthermore, unless otherwise required by context, singular terms may include pluralities and plural terms may include the singular. A list of abbreviations used herein is as follows: Ab: antibody; CDRs: complementarity determining regions; $C_H$: heavy-chain constant domain; $C_L$: light-chain constant domain; PBS: phosphate buffered saline; PCR: polymerase chain reaction; scFv: single-chain variable fragment; $V_L$: light-chain variable domain; $V_H$: heavy-chain variable domain; HA: hemagglutinin; HAI: inhibition of hemagglutinination; mAb: monoclonal antibody; hmAb: human monoclonal antibody.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. These techniques and procedures are generally performed according to conventional methods well known in the art and as described in various general and more specific references that are cited and discussed throughout the present specification. See e.g., Sambrook et al., Molecular Cloning: A Laboratory Manual (3rd ed., Cold Spring Harbor Laboratory Press, Cold Spring Harbor, N.Y. (2001).

As used herein, the term "antibody" refers generally and broadly to immunoglobulins, monoclonal antibodies, and polyclonal antibodies, as well as active fragments thereof. The fragment may be active in that it binds to the cognate antigen (e.g., HA or a virus).

As used herein, the term "human antibody" refers to an antibody in which substantially every part of the protein is substantially non-immunogenic in humans, with no or only minor sequence changes or variations, as compared with native human antibodies.

An antigen binding site is generally formed by the heavy chain variable region (VH) and the light chain variable region (VL) immunoglobulin domains, with the antigen-binding interface formed by six surface polypeptide loops, termed complimentarity determining regions (CDRs). There are three CDRs each in VH (HCDR1, HCDR2, HCDR3) and VL (LCDR1, LCDR2, LCDR3), together with framework regions (FRs) between or surrounding the CDRs.

The term "CDR region" or "CDR" means the hypervariable regions of the heavy or light chains of the immunoglobulin as defined by Kabat et al., 1991 (Kabat, E. A. et al., (1991) Sequences of Proteins of Immunological Interest, 5th Edition. US Department of Health and Human Services, Public Service, NIH, Washington), and later editions. An antibody typically contains 3 heavy chain CDRs and 3 light chain CDRs.

A binding fragment of an antibody of the invention may be a Fab, a Fab', a F(ab')$_2$, or a scFv fragment. The binding fragments of an antibody can be obtained by a variety of methods, including, digestion of an intact antibody with an enzyme, such as pepsin (to generate (Fab')$_2$ fragments) or papain (to generate Fab fragments); or de novo synthesis. Antibody fragments can also be synthesized using recombinant DNA methodology. See, e.g., Fundamental Immunology (Paul ed., 4d ed. 1999); Bird, et al., Science 242:423 (1988); and Huston, et al., Proc. Natl. Acad. Sci. USA 85:5879 (1988).

DETAILED DESCRIPTION OF THE INVENTION

Embodiments of the invention relate to anti-H1N1 antibodies or fragments thereof. The antibodies of the invention may be generated using molecular biology techniques by screening immortalized memory B cells from healthy donors without the need for prior vaccination. Fragments of these antibodies may include Fab, scFv, F(ab')$_2$, etc. Antibodies of the invention have high viral neutralizing efficacies.

In accordance with embodiments of the invention, neutralizing antibodies against H1N1 viruses may be identified with a process shown in FIG. 1, which is similar to the process used in Hao Wang et al mentioned above. However, the memory B cells may be from healthy donors who need not have been vaccinated with PANFLU.1. As shown, the first step 11 involves isolating memory B cells from donors. The donors are healthy donors with or without prior exposure to the H1N1 virus or vaccines. The isolated memory B cells are then immortalized with EBV (step 12). Then, the EBV-immortalized B cells are screened for their abilities to secret antibodies that can bind to hemagglutinin (HA) and/or inhibit HA activity (i.e., hemagglutination) (step 13). Finally, the memory B cells identified in step 13 are further screened for their abilities to secret antibodies that can neutralize the viruses (step 14).

Using the protocols described above, a large number (20160 single B cell clones) of immortalized memory B-cell clones were screened. As result of this screening, several clones that can bind HA and/or inhibit HA activities were identified. Among these, one hmAb (32D6) was identified that has good binding affinity to hemagglutin (HA), viral neutralizing capacities and hemagglutination inhibition (HAI) activities against the 2009 pandemic H1N1 virus. The standard name for the H1N1 2009 pandemic strain is A(H1N1)pdm09, according to the recommendation of WHO.

The hmAb 32D6 secreted by the isolated clone of immortalized memory B cells was purified and the purity of the hmAb 32D6 was checked by SDS-PAGE. As shown in FIG. 2(A), Coomassie staining revealed that the recombinant antibody is relatively pure and its relative molecular weight is similar to that of human IgG (hIgG). FIG. 2(B) shows Western blot analysis of the purity of mAb 32D6. The Western blot analysis was performed using a goat anti-human IgG antibody fragment (F(ab')$_2$ fragment from Jackson Lab), which was affinity purified. This F(ab')$_2$ fragment is specific for IgG and is conjugated with horseradish peroxidase.

The HA binding affinity of hmAb 32D6 was assessed using surface plasmon resonance (Biacore T200). Briefly, hmAb 32D6 antibody was immobilized on CM5 chips at a density that allowed one to achieve $R_{max}$ in the range of 0-500 Response Units (RU). In this example, the kinetic assay parameters were as follows: data collection rate 1 Hz; dual detection mode; temperature: 25° C.; and concentration unit: nM. Serial dilutions of hemagglutinin (HA) in the running buffer were flowed into the system to bind with the hmAb 32D6 antibody. These afforded binding kinetic parameters. Then, the HA-antibody complex was washed by flowing buffer into the system to derive the dissociation kinetic parameters.

The results were evaluated with the BIAcoreT200 evaluation software. The binding responses were corrected for buffer effects by subtracting responses from a blank flow cell. A 1:1 Langmuir fitting model was used to estimate the $k_a$ or $k_{on}$ (association rate or on-rate) and $k_d$ or $k_{off}$ (dissociation rate or off-rate). The $K_D$ (or $K_d$) values may be determined from the ratios of $k_{off}$ and $k_{on}$ (i.e., $K_D=k_{off}/k_{on}$).

Figure 6:
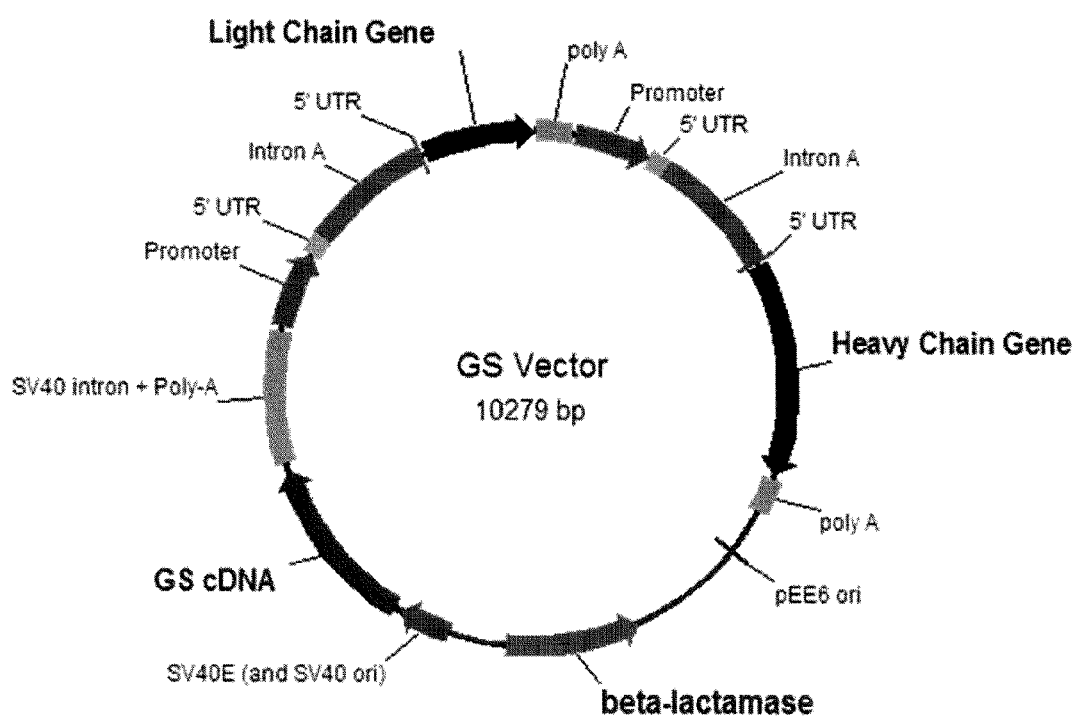
FIG. 6 shows a map of an expression vector, pXC-17.4, in accordance with one embodiment of the invention.
Figure 7A:
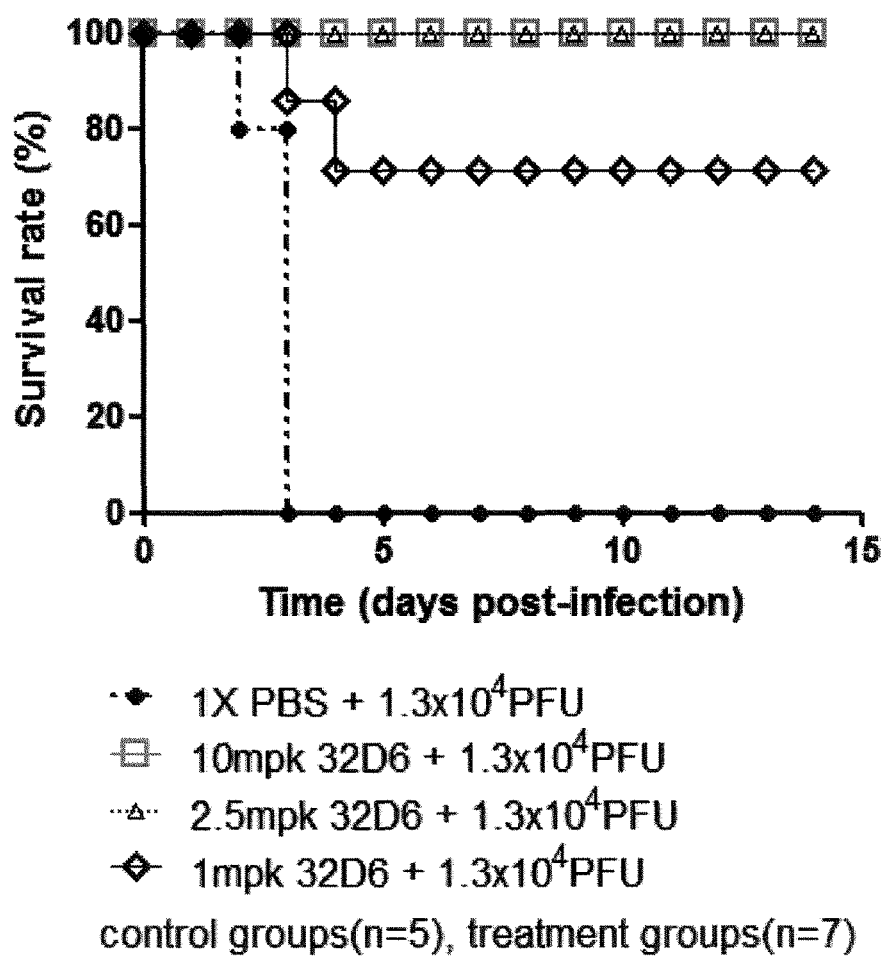
FIG. 7(A) shows prophylactic effects of 32D6 in preventing H1N1 virus infection in animal models in accordance with one embodiment of the invention.
Figure 7B:
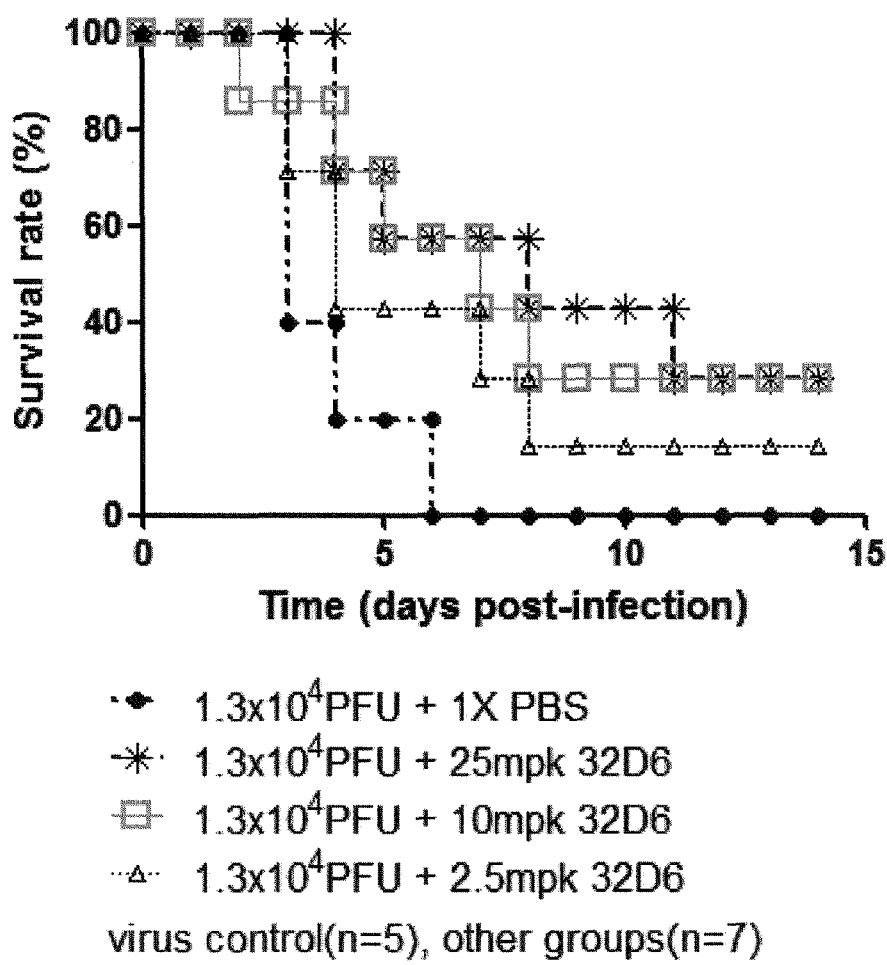
FIG. 7(B) shows the treatment effects of 32D6 in preventing H1N1 virus infection in animal models in accordance with one embodiment of the invention.

As shown in FIG. 2(C), 32D6 is found to have a very high affinity for HA. In this example, the $K_D$ of 32D6 is found to be in the range of $10^{-10}$ M or better. Other clones were also identified, but were found to have lower affinities.

The hmAb 32D6 is effective in neutralizing H1N1 virus activity. As shown in FIGS. 3(A)-3(C), at 2,000 PFU per well (1×10$^4$ MDCK cells per well in 384-well format plate, greiner, Germany), H1N1 virus infects cells with high efficiency (FIG. 3(B)). However, in the presence of 0.01 µg/well hmAb 32D6, infection of the cells by 2,000 PFU/well H1N1 virus was completely prevented (FIG. 3(C)). FIG. 3(A) shows the cells without the virus or mAb as a control. These results indicate that hmAb 32D6 is very effective in neutralizing the activity of H1N1, even at a low concentration (0.01 µg/well).

Figure 4B:
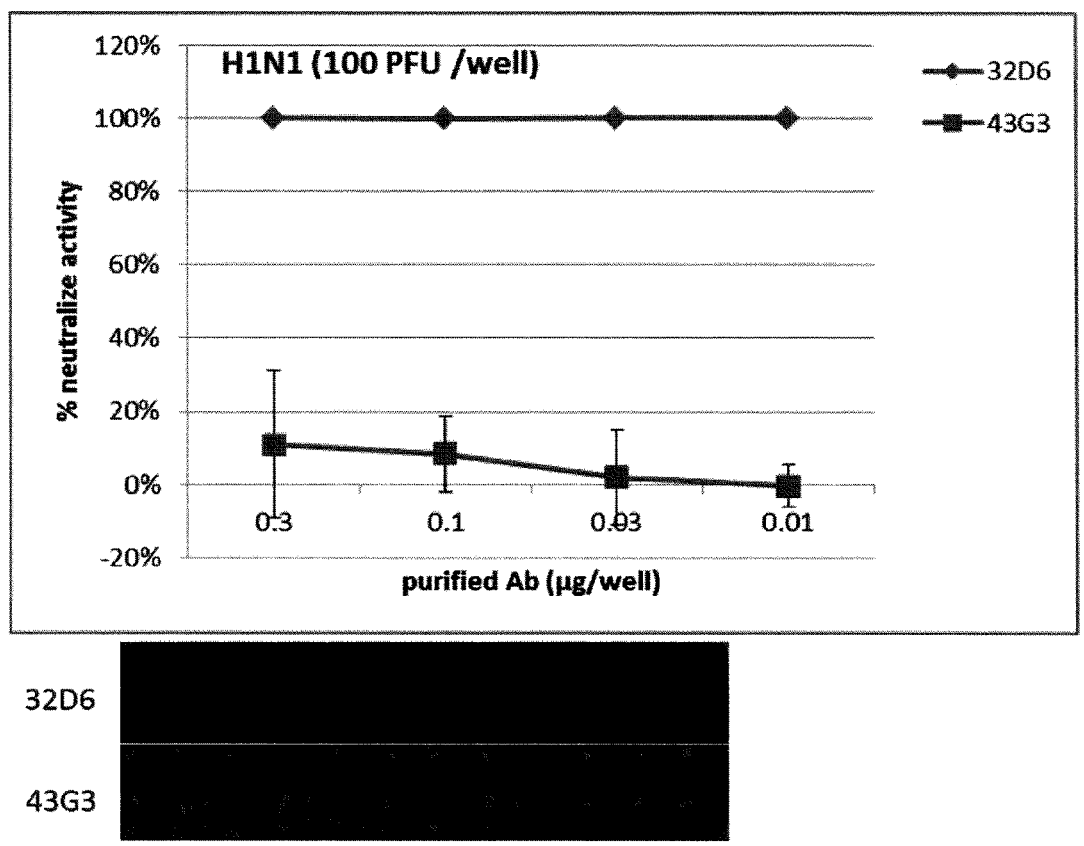
FIG. 4(B) shows a comparison of the activity of 32D6 in neutralizing virus infection of cells, as compared with another antibody 43G3, in accordance with embodiments of the invention.
Figure 4C:
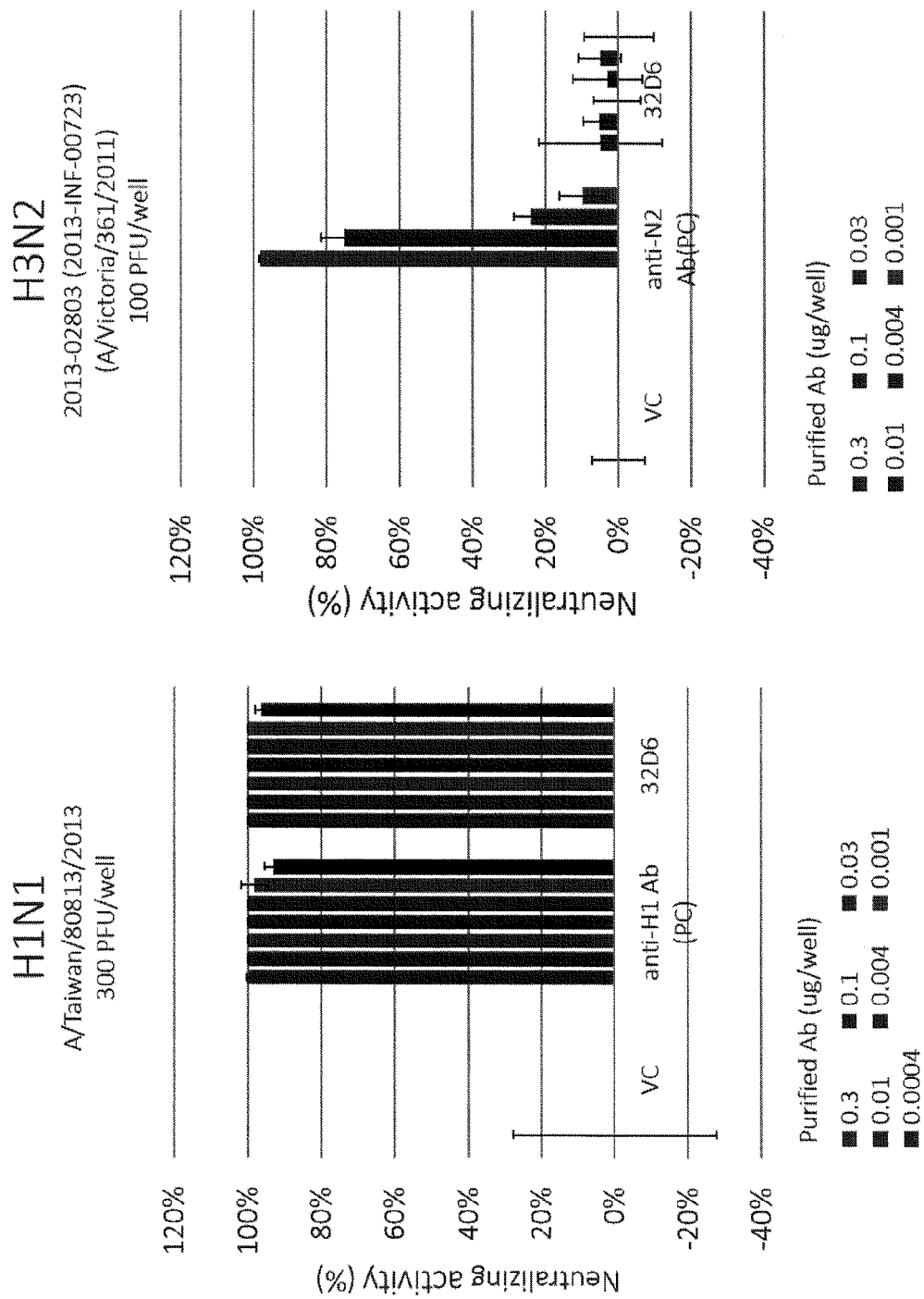
FIG. 4(C) shows the selectivity for H1N1 by 32D6.
Figure 4D:
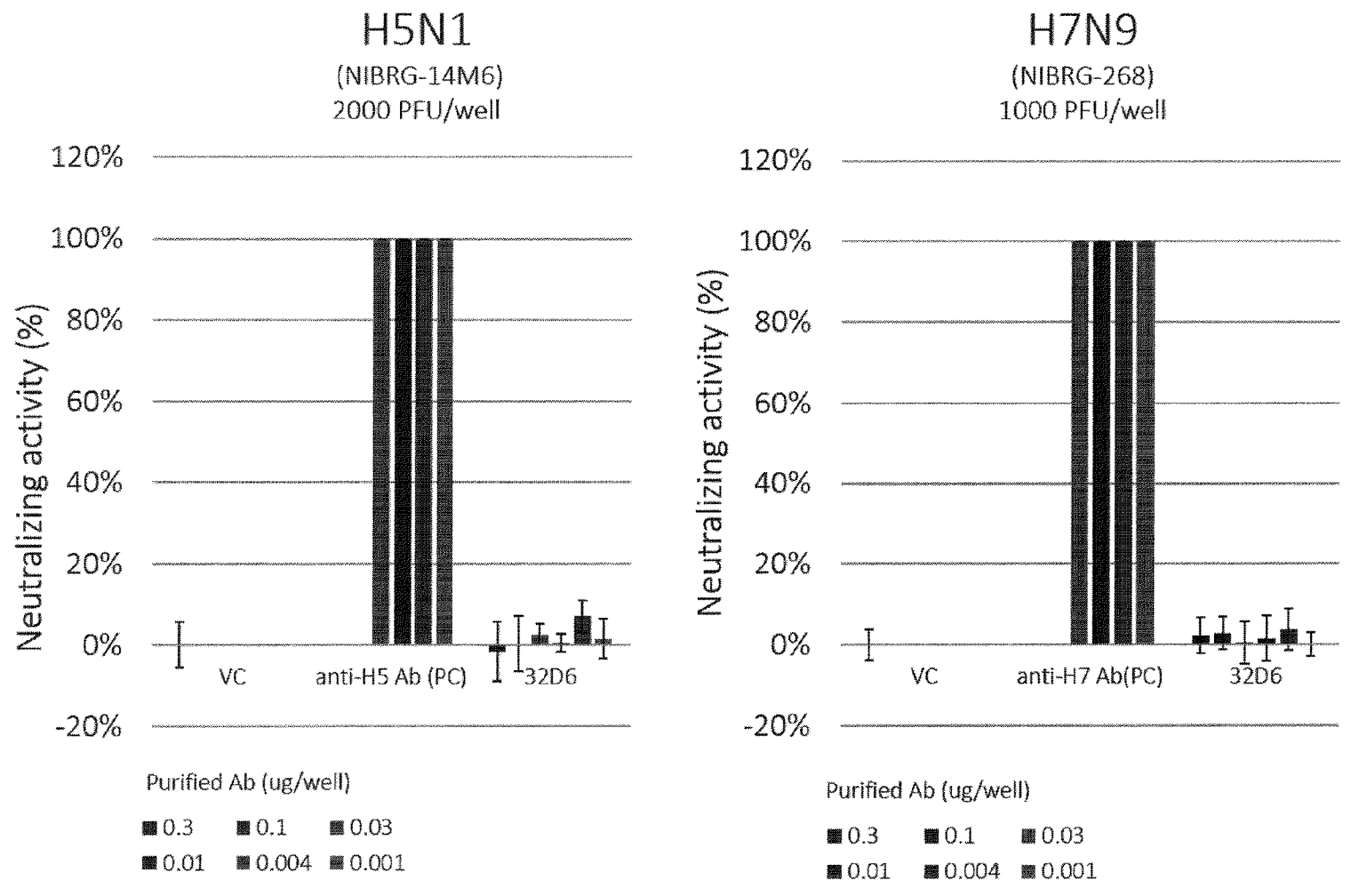

To quantify the efficacy of hmAb 32D6 in neutralizing H1N1, the neutralizing assays were further performed using various concentrations of hmAb 32D6 and 2,000 PFU/well H1N1 in a cell invasion assay using MDCK cells as described above. A virus control (without adding hmAb 32D6) is shown as a control. As shown in FIG. 4(A), hmAb 32D6 is found to completely neutralize the activity of H1N1 at a concentration of 0.003 µg/per well. Based on the results from the extents of neutralization as a function of hmAb 32D6 concentrations, the IC$_{50}$ value is estimated to be around 0.001 µg/well. In contrast, another clone mAb 43G3 is barely effective in neutralizing H1N1 viruses even at high concentrations (FIG. 4(B)).

This antibody, hmAb 32D6, is specific for H1N1. As shown in FIGS. 4(C) and 4(D), 32D6 is very effective in neutralizing the activities of H1N1. However, it is not effective in neutralizing H3N2 (FIG. 4(C)), H5N1 or H7N9 (FIG. 4(D)). This specificity indicates that the antibody likely recognize epitope(s) on HA that are unique to the H1N1 strain.

Figure 4E:
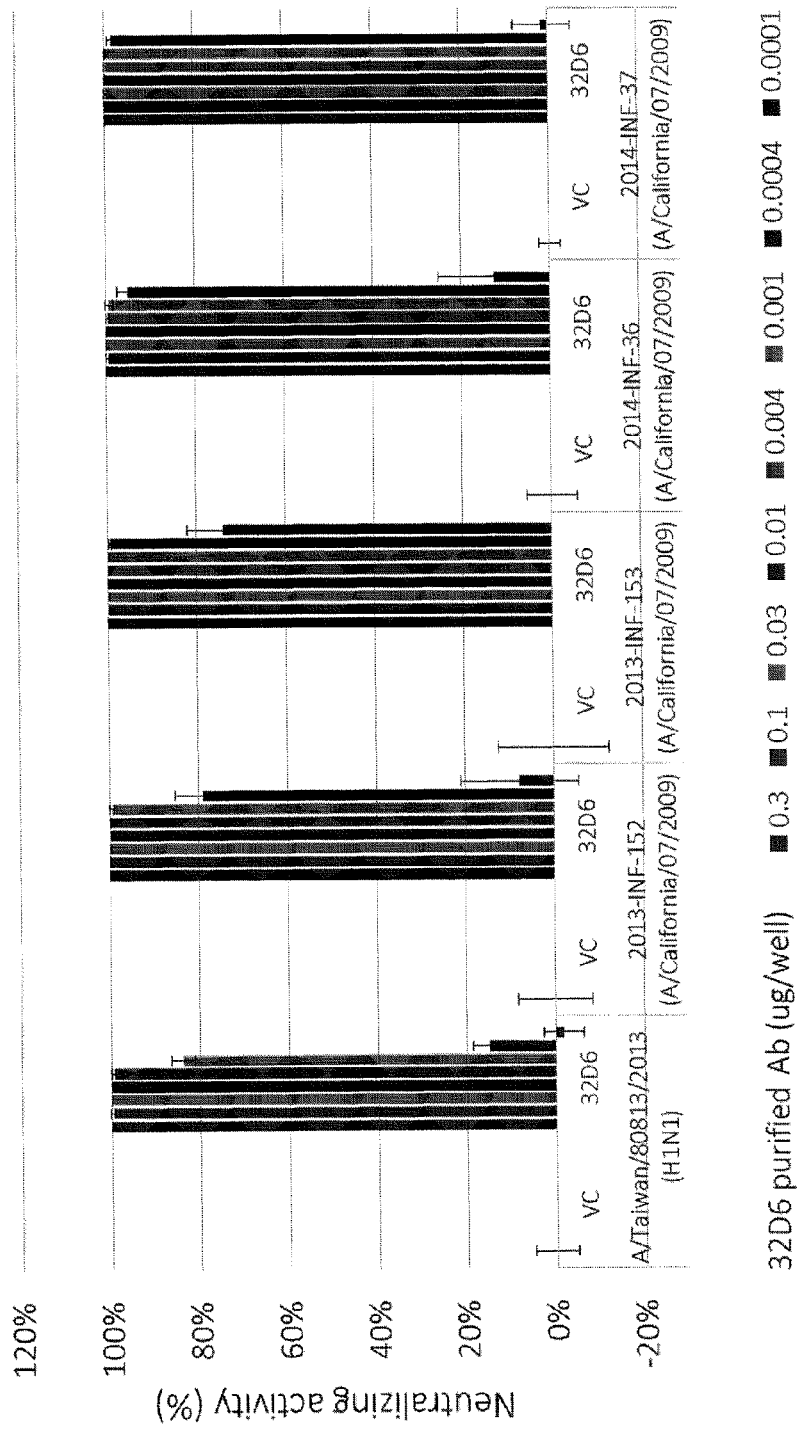
FIG. 4(E) shows that 32D6 is effective in neutralizing post pandemic (2009) strains of H1N1 viruses.
Figure 4F:
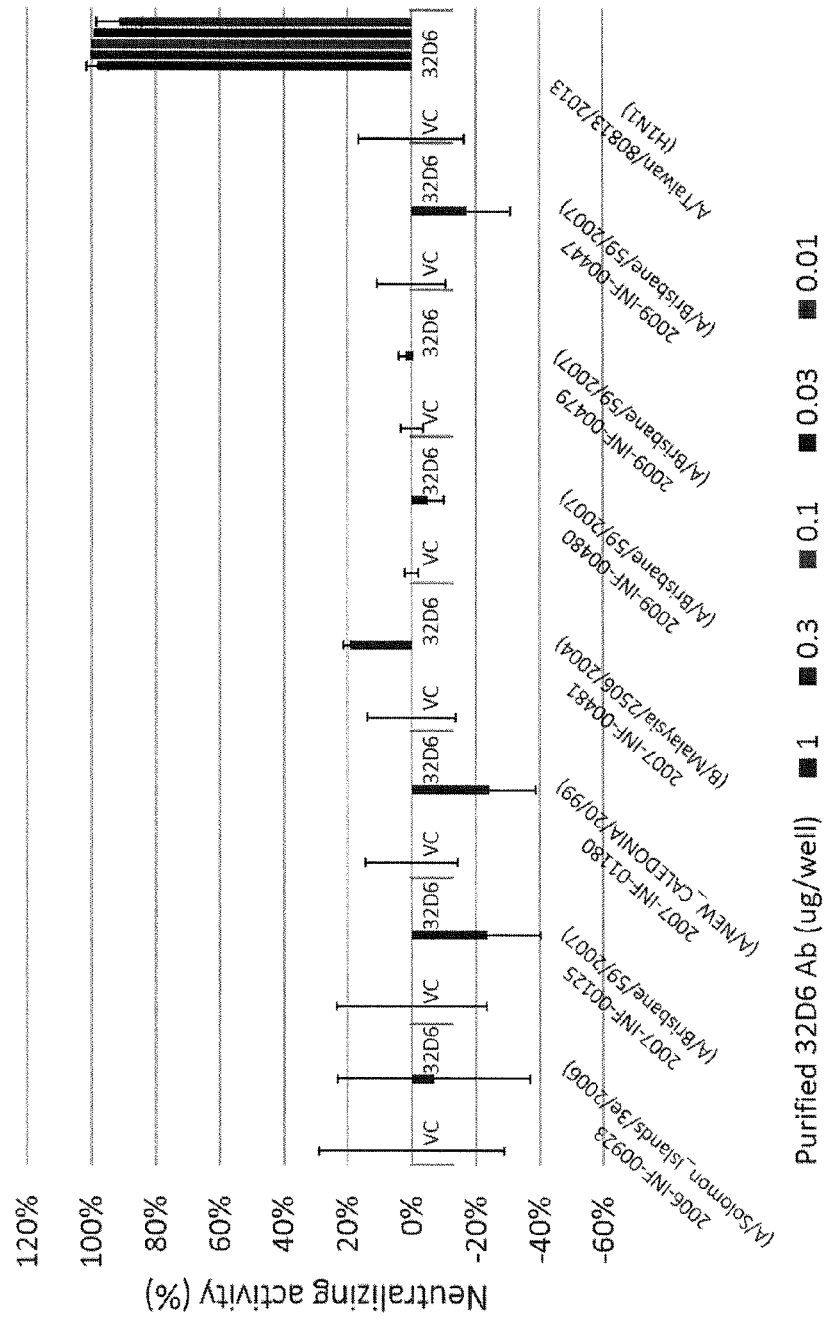
FIG. 4(F) shows that 32D6 is not effective in neutralizing pre-pandemic (2009) strains of H1N1 viruses.

In addition to being highly effective in neutralizing H1N1 virus of the 2009 pandemic strain, hmAb 32D6 was also found to be highly specific for H1N1 strains post 2009 pandemic (FIG. 4(E)). In contrast, hmAb 32D6 is not effective against the pre-2009 H1N1 strains (FIG. 4(F)). This impressive selectivity is not expected even though the recombinant HA used for the screening was derived from the ectodomain DNA fragment of A/Sichuan/1/2009 (H1N1) HA gene. This unexpected selectivity likely arises from a new epitope that did not exist in H1N1 viruses prior to 2009. Preliminary data from our attempts to locate the epitope suggest that the epitope may be located from around residue 189 to around residue 272 of HA.

The native human Ab gene (8B4) corresponding to hmAb 32D6 was cloned and sequenced. The nucleotide sequence (SEQ ID NO: 1) and amino acid sequence (SEQ ID NO: 2) of the heavy chain of 8B4 gene are shown in FIG. 5(A) and FIG. 5(B), respectively. The nucleotide sequence (SEQ ID NO: 3) and amino acid sequence (SEQ ID NO: 4) of the light chain of 8B4 gene are shown in FIG. 5(C) and FIG. 5(D), respectively. In these sequences, the CDR sequences are underscored. The six CDR sequences of 32D6 are shown in FIG. 5(E): SEQ ID NOS: 5-10.

Using the 8B4 gene sequence, expression vectors may be constructed. One skilled in the art would appreciate that any suitable expression vectors may be used. For example, the Lonza GS System pXC-17.4 plasmid (Lonza Group, Basel, Switzerland) may be used in conjunction with a glutamine synthase (GS) knockout host cell. Using the pXC-17.4 plasmid and a GS Chinese Hamster Ovary (CHO) cell line from Lonza, a recombinant human monoclonal antibody (rhmAb) (8B4) has been obtained.

For example, FIG. 6 shows an example of a pXC-17.4 vector that may be used to expression an antibody of the invention. In addition, any expression vector of the invention may be transfected into a suitable host cell, such as a mammalian cell, a yeast cell or an insect cell.

This rhmAb was found to have identical antibody properties as those of the native hmAb (32D6), with respect to the binding affinity, virus neutralizing activities, and HAI activities. These results indicate that the viral binding and neutralizing function of antibody 32D6 are not affected by glycosylation (or different glycosylation) in CHO cells.

One skilled in the art would appreciate that as long as the CDR sequences are retained, the antibody activities can be preserved. Thus, in addition to hmAb 32D6, any antibodies (e.g., recombinant antibodies) or binding fragments thereof would have the same binding specificity and similar affinities. That is, useful antibodies are not limited to hmAb 32D6 itself, but can also include other antibodies or binding fragments thereof (e.g., Fab fragment, F(ab')2 fragment, single-chain Fv (scFv), etc.) that retain the same binding. For examples, such fragments containing the same CDR sequence are likely to retain the binding. The CDR sequences of 32D6 are summarized in the table shown in FIG. 5(E) with their SEQ ID NOs: 5-10 are also shown.

The hmAb 32D6 has tight binding to HA and high activity in neutralizing H1N1 virus. Therefore, this hmAb should be useful in preventing or treating H1N1 infections. The effectiveness of 32D6 in preventing and treating H1N1 infections is assessed with the in vivo tests.

In pharmacodynamic (PD) evaluation using an animal model, passive immunization with 32D6 displayed anti-H1N1 efficacy in in vivo protection, both prophylactically and therapeutically, against a lethal viral challenge in mice. Therefore, hmAb 32D6 may have important clinical implications for passive immune therapy of infected patients with severe respiratory syndrome, especially children, the elderly and immunodeficient individuals.

Embodiments of the invention will be further illustrated with the following examples with specific experimental procedures. One skilled in the art would appreciate that these examples are for illustration only and are not meant to limit the scope of the protection.

EXAMPLES

Cell Cultures and Virus Preparation

The marmoset B-lymphoblastoid cell line B95-8 and 293T cells were cultured in RPMI 1640 medium containing L-glutamine (Invitrogen, Carlsbad, Calif., USA) supplemented with 10% fetal calf serum (FCS) and penicillin-streptomycin at 37° C. in a humidified incubator with 5% $CO_2$. Madin-Darby canine kidney (MDCK) cells were cultured in DMEM medium (Invitrogen) supplemented with 10% FCS. *Spodoptera frugiperda* (Sf9) cells were maintained in Sf-900 II SFM (Invitrogen).

H1N1 virus was generated by Medigen Vaccine Biologics Co. (MVC, Taiwan). Influenza A virus A/California/7/2009 NYMCX-179A (H1N1), this strain is a pandemic vaccine strain recommended for use in vaccine development. Other influenza virus clinical strains are provided by Taiwan CDC and used for neutralizing assay in this patent application, 2013-80813 (A/Taiwan/80813/2013 (H1N1)), 2013-INF-152(2013-00586; A/California/07/2009), 2013-INF-153 (2013-01141; A/California/07/2009), 2014-INF-36(2014-03006; A/California/07/2009), 2014-INF-37(2014-04001; A/California/07/2009), 2006-INF-00923 (925; A/Solomon-_Islands/3e/2006), 2007-INF-00125 (A/Brisbane/59/2007), 2007-INF-01180 (A/NEW_CALEDONIA/20/99), 2009-INF-00480(A/Brisbane/59/2007), 2007-INF-00481 (180; B/Malaysia/2506/2004), 2009-INF-00479(A/Brisbane/59/2007), 2009-INF-00447(A/Brisbane/59/2007). Other influenza viruses used for neutralization assay are: the vaccine strain NIBRG-14M6 (H5N1), the vaccine strain NIBRG-268 (H7N9) and the clinical strain provided by Taiwan CDC 2013-INF-00723 (2013-02803; A/Victoria/361/2011 (H3N2)). Propagation of those influenza virus clinical strains, and determination of the 50% tissue culture infectious dose ($TCID_{50}$) were performed in Madin-Darby canine kidney (MDCK) cells according to Reed-Muench method.

Purification of Human Memory B Cells

Peripheral blood memory B cells were isolated using a magnetic isolation kit (Miltenyi, Bergisch Gladbach, Germany) as described in A. Henn et al., "*Modulation of single-cell IgG secretion frequency and rates in human memory B cells by CpG DNA, CD40L, IL-21, and cell division*," J. Immunol., (2009), 183: 3177-3187. Briefly, peripheral blood mononuclear cells (PBMCs) were isolated from healthy donors, including vaccinated donors and unvaccinated healthy donors. Non-memory B cells in PBMCs (such as T cells, natural killer cells, monocytes, dendritic cells, granulocytes, platelets and erythroid cells) were removed using biotinylated antibodies against CD2, CD14, CD16, CD36, CD43 and CD235a (glycophorin A), followed by binding with anti-biotin microbeads. After removal of the non-memory B cells, memory B cells may be isolated by magnetic labeling of memory B cells with CD27 microbeads, followed by isolation of the magnetically labeled cells.

The identity and purity of these memory B cells may be assessed using any methods known in the art, such as flow cytometry. For example, the isolated memory B cells, which are CD19+ and CD27+, may be labeled with a surface-staining antibody, such as FITC-conjugated CD27 or PE-conjugated CD19 (Miltenyi Biotech). The stained cells are then analyzed with a flow cytometer. The data may be analyzed using any suitable program, such as CellQuest software (BD, USA).

EBV Preparation and Immortalization of Peripheral Blood Memory B Cells

EBV for immortalization of human B lymphocytes was prepared from B95-8 cells, as described in E. James et al., "*Growth of B*95-8 *cells and expression of Epstein-Barr Virus lytic phase in serum-free medium*," J. Virol. (1987) 61: 4033-4037. For example, B95-8 cells were cultured at a density of $10^6$ cells/ml in RPMI 1640 with 10% (v/v) FCS at 37° C. in 5% $CO_2$. The supernatant was collected and filtered with a sterile filter (0.45 μm; Millipore, Billerica, Mass., USA). The cells may be stored in aliquots in liquid nitrogen.

Peripheral blood memory B cells were EBV-transformed according to the protocol, as described in E. Traggiai et al., "An efficient method to make human monoclonal antibodies from memory B cells: potent neutralization of SARS coronavirus," Nat. Med. (2004) 10: 871-875.

Briefly, allogenic mononuclear cells ($5\times10^5$ cells/ml) in RPMI 1640 medium without sera were irradiated by 35 Grey $Co^{60}$ and plated in 96-well plates (50 000 cells/100 μl per well) in 30% FCS. These irradiated cells were used as feeding cells. Memory B cells were then sorted into a single cell per well into 96-well plates with feeding cells, before the addition of 50 μl mixture per well containing 48 μl of EBV suspension, 1 μl of cyclosporine A solution (at the final concentration of 400 ng/ml) and 1 μl of CpG 2006 (at final concentration of 2.5 μg/ml). After EBV transformation, immortalized memory B-cell clones were expanded for 28 days with medium changed every 3-5 days. The supernatant of each clone (100 μl) was used to screen for positive clones specific for 2009 pandemic (H1N1) HA.

Expression of Recombinant HA Proteins (rHAs)

Recombinant hemagglutinins (rHAs) were expressed and purified using the Baculovirus/insect cell system (BD Biosciences, San Diego, Calif., USA), as described in Z. Li et al., "*Serologic cross-reactivity among humans and birds infected with highly pathogenic avian influenza A subtype H5N*1 *viruses in China*," Immunol. Lett. (2011) 135: 59-63. Briefly, the HA ectodomain DNA fragment of A/Sichuan/1/2009 (H1N1) HA gene was cloned into the transfer vector FastBac (Invitrogen). Recombinant baculovirus genomes were transfected into Sf9 cells for the generation of recombinant baculoviruses. Viral supernatant was collected at 72 h post-infection. rHAs were expressed after three rounds of infection and purified using Ni-NTA chromatography (GE Healthcare, Pittsburgh, Pa., USA). Western blotting confirmed the expression and purification of rHAs with anti-His or anti-HA antibodies.

Enzyme-Linked Immunosorbent Assay (ELISA)

ELISAs were performed using a 96-well plate (Maxisorb, Nunc) to measure the HA-binding activities of sera from donors or hmAbs from immortalized memory B cells, as described in Z. Li et al., "*Serologic cross-reactivity among humans and birds infected with highly pathogenic avian influenza A subtype H5N1 viruses in China*," Immunol. Lett. (2011) 135: 59-63. Briefly, ELISA was performed with reagents consisting of: (1) inactivated whole H1N1 virus (diluted in 10 µg/ml), manufactured by MVC; (2) serial dilutions of monoclonal antibodies; (3) goat anti-mouse IgG Ab (γ-chain specific,) conjugated with horseradish peroxidase (Jackson ImmunoResearch Laboratories, INC. USA); and (4) TMB substrates (3,3',5,5'-Tetramethylbenzidine, Sigma). Inactivated H1N1 virus were coated on polystyrene plates at 4° C. overnight followed by blocking with 5% bovine serum albumin (Invitrogen) at 37° C. for 2 h. The sera/supernatants from donors/b cells at serial of dilution were incubated in wells at 37° C. for 2 h. After complete wash, detection antibody, anti-human IgG with horseradish peroxidase-labeled (dilution in 1:5000) was added at 37° C. for 1 h. The TMB/$H_2O_2$ was added to develop color, and the reaction was stopped with 50 µl of $H_2SO_4$. The amount of chromogen produced was measured based on absorbance at 410 nm and 630 nm using an ELISA reader (SpectraMax, MD, US). The clones that bind to the inactivated H1N1 viruses in the above ELISA assays were further confirmed using recombinant HA (rHA) as the ligand in a second ELISA assays.

Neutralization Assays—Activity Determined by High Content Image System

Neutralization assays of sera or hmAbs were performed with methods known in the art and modified according to procedures known in the art, see Z. Li Z et al., "*Identification of amino acids in highly pathogenic avian influenza H5N1 virus hemagglutinin that determine avian influenza species specificity*," Arch. Virol. (2011), 156: 1803-1812. Briefly, MDCK cells were pre-cultured in DMEM-base serum free medium containing 1% P/S, 1% BSA, 25 mM HEPES and 2 ug/ml TPCK-trypsin before neutralizing assay. Serial dilutions of sera, cell culture supernatant, or purified 32D6/8B4 hmAbs were incubated with H1N1 (A/Taiwan/80813/2013 (H1N1)) viruses for 2 hour at 37° C. before the mixture was added to MDCK cells $1 \times 10^4$ per well in 384-well plates (Greiner, Germany). Following 60 mins co-culture, MDCK cells were washed with PBS to remove supernatant containing free antibodies and virus, and then replaced with 10% FBS DMEM-base complete medium for another 16 hours culture at 37° C. Consequentially, MDCK cell were fixed with 4% Paraformaldehyde (PFA) and performed intracelluar and nucleus co-staining with anti-NP-FITC labeled antibody (Millipore MAB8257F) and DAPI (SIGMA-B2261). Infection efficiency was quantified and analyzed with a high content image system (ImageXpress Micro, Molecular Device, Sunnyvale, Calif., USA). The neutralization activity of hmAbs was measured according to the equation: $(A-B)/A \times 100\%$, wherein 'A' represents the cell counts of positive wells that contained only H1N1 or other flu virus strains, and 'B' represents the value of wells that contained the mixture of testing serum samples and H1N1 or other flu virus strains.

Construction of Expression Vectors

The nucleotide sequences of SEQ ID NOs: 1 and 3, which code for the amino acid sequences of the heavy chain and light chain, respectively, of hmAb 32D6, were cloned from the isolated memory B cell clone. These nucleotide sequences were inserted into a suitable cloning vector, having restriction sites for cloning these genes into an expression vector.

The cloning vector containing antibody gene was digested with restriction enzymes (e.g., HindIII and EcoRI) for cloning into an expression vector for the expression of the antibody. Any suitable expression vectors may be used, such as the Lonza GS System pXC-17.4 plasmid (Lonza Group, Basel, Switzerland). Suitable vectors may include a promoter (e.g., a viral promoter, mCMV) and contain gene-optimized antibody constant regions. In addition, a suitable may contain a selectable marker. For example, the expression plasmid, pXC-17.4, links the expression of an exogenous protein to the glutamine synthetase (GS) gene. The pXC-17.4 vector may be used with a GS knock-out host cells to facilitate selection of the transfected cells.

Once the antibody gene insert was cloned into the pXC-17.4 vector, individual bacterial colonies were selected for sequence analysis. The plasmids are verified for proper sequence and proper orientation within the plasmid using primers that are situated outside the ORF of the antibody. Based on this information, one single clone is selected for scale-up and generation of a sufficient quantity of plasmid for transfection of CHO cells.

The GS Chinese Hamster Ovary (CHO) cell lines are used, which have mutations in both copies of the GS gene, so that they require the expression of GS on the pXC-17.4 expression plasmid for survival in the absence of glutamine, an amino acid that is essential for growth. For plasmid transfection, GS CHO cells were thawed into appropriate media formulation under no selection, i.e., containing L-glutamine. CHO cells were maintained at 5% $CO_2$ in a 37° C. incubator.

Transfection of GS CHO cells with the pXC-17.4 expression vector was performed using electroporation. For example, cells may be electroporated by delivering a single pulse of 300V, 900 uF with resistance set to infinity Immediately after electroporation, each batch of cells was added to a flask containing the appropriate media. Cells were gently mixed and incubated overnight in a cell culture incubator. The next day, cells were centrifuged to remove media containing plasmid.

When cell numbers reach about $0.6 \times 10^6$ cells per mL, cells were expanded into selection media. After two weeks in selection, individual colonies of CHO cells were selected based on growth on transwell plates. Individual colonies were assessed based on growth and productivity characteristics, through scale-up.

The quantity and integrity of product may be assayed by protein A affinity chromatography and monitored with absorbance at 280 nm, by ELISA, or by SDS-PAGE analysis.

Host Cells

Expression vectors in accordance with embodiments of the invention may be expressed in any suitable cells. As noted above, when using pXC-17.4 expression plasmids, it is convenient to use a GS knockout host cells to facilitate selection of transfected cells. CHOK1SV GS Knockout (KO) host cell line (from Lonza) is a derivative of Lonza's suspension adapted CHOK1SV host cell line. In this new GS-KO cell line, both alleles of the endogenous glutamine synthetase gene have been "knocked out," leading to a requirement for exogenous glutamine.

Purification of 32D6/8B4 and Western Blot rHAs and purified 32D6/8B4 monoclonal Ab were resolved using SDS-polyacrylamide gel electrophoresis and electrophoretically transferred to a nitrocellulose membrane. After blocking with 5% BSA, the blots containing rHA were probed with anti-His-tag mouse MAbs at room temperature for 1 h. After a complete wash, horseradish peroxidase-conjugated anti-mouse IgG was added and incubated at room temperature for 0.5 h before rHA protein detection with the West Pico Chemiluminescent Substrate (Thermo Scientific, Rockford, Ill., USA). The blots containing 32D6/8B4 antibodies were directly probed with goat anti-mouse IgG Ab (γ-chain specific, USA) conjugated with horseradish peroxidase (Jackson ImmunoResearch Laboratories, INC.) and detected with West Pico Chemiluminescent Substrate.

In Vivo Protection Experiments

All animal experiments were conducted in accordance with ethical procedures and policies approved by an appropriate Institutional Animal Care and Use Committee. DBA/1 mice (average body weight 20 g) were randomly separated into different groups: the control group (5 mice) and three treatment groups (7 mice each). Mice were anesthetized by intraperitoneal administration of isoflurane and challenged with viruses (H1N1-TW80813).

To evaluate the prophylactic efficacy of the mAb 32D6, mice were injected intravenously with PBS (control) or the mAb 32D6. Each mouse in the control group received an equal volume (e.g., 50 µl/mouse) of PBS, and the mice in the three treatment groups each received 10 mpk (mg/Kg body weight) 32D6, 2.5 mpk 32D6, or 1 mpk 32D6, respectively. After 1 hour, the mice were anesthetized with isoflurane. Then, the mice were challenged with the virus (H1N1-TW80813; $1.3\times10^4$ PFU in 50 μl/mouse) via intranasal injection or inhalation. After the virus challenge, animals were observed and recorded daily for mortality, morbidity, body weight and facial expression for up to 14 days after infection.

As shown in FIG. 7(A), all mice in the control group died within 3 days after the virus challenge. In contrast, all mice in the treatment groups receiving 10 mpk and 2.5 mkp antibodies survived beyond 14 days. One mouse in the treatment group with 1 mpk antibody died in 3 days and the other died in 4 days, while the remaining 5 mice survived beyond 14 days. These results clearly show that mAb 32D6 of the invention is effective in preventing H1N1 infection.

To determine the therapeutic efficacy of the mAbs, mice were anesthetized with isoflurane, followed by intranasal injection (or inhalation) of the virus (H1N1-TW80813; $1.3\times10^4$ PFU in 50 μl/mouse). After 24 hours, each mouse in the control group received an equal volume (e.g., 50 μl/mouse) of PBS, and the mice in the three treatment groups each received 25 mpk (mg/Kg body weight) 32D6, 10 mpk 32D6, or 2.5 mpk 32D6, respectively. Animals were observed and recorded daily for mortality, morbidity, body weight and facial expression for up to 14 days after infection.

As shown in FIG. 7(B), all mice in the control group died within 6 days. In contrast, 2 mice each in the treatment groups receiving 25 mpk and 10 mkp antibodies survived beyond 14 days, and one mouse in the treatment group with 1 mpk antibody survived beyond 14 days. These results clearly show that mAb 32D6 of the invention is effective in treating H1N1 infection.

Statistical Analysis

For survival, probability was calculated using Fisher's exact test, comparing the rate of survival of mice treated with specific mAbs with those of the control groups.

Advantages of embodiments of the invention include one or more of the following. Embodiments of the invention can use memory B cells from any donor, with or without prior infection or vaccination. By not limiting to donors who had prior vaccination or donors who have been infected by the viruses and have since recovered, the donor population for use with embodiments of the invention is more diverse. Starting from a more diverse population of B cells, embodiments of the invention are more likely to identify antibodies that represent the best unbiased sequences in the naïve immune repertoire. In addition, because there is no need to wait for the development of a vaccine or infected donors, embodiments of the invention can be used to identify antibodies for passive immunotherapy at the moment of an outbreak of any virus.

In contrast, prior art methods rely on having a vaccine to vaccinate a donor or rely on patients who had been infected by the virus. These prior art methods cannot be used immediately after an outbreak. In addition, relying on donors who had been vaccinated or infected with the virus would result in a more limited population of the memory B cells. The limited population of memory B cells might be biased due to individual variations in the immune responses of the particular donors.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A monoclonal antibody, or an antigen binding fragment thereof specifically binding influenza virus H1N1 protein, comprising a heavy chain variable region and a light chain variable region,
   wherein the heavy chain variable region comprises complementarity determining regions (CDR) having the amino acid sequences of SEQ ID NO: 5, SEQ ID NO: 6, and SEQ ID NO: 7; and wherein the light chain variable region comprises complementarity determining regions having the amino acid sequences of SEQ ID NO: 8, SEQ ID NO: 9, and SEQ ID NO: 10.

2. The monoclonal antibody, or the antigen binding fragment thereof, according to claim 1, wherein the antibody comprises a heavy chain having the amino acid sequence of SEQ ID NO: 2 and a light chain having the amino acid sequence of SEQ ID NO: 4.

3. The monoclonal antibody, or the antigen binding fragment thereof, according to claim 1, wherein the H1N1 virus is a 2009 strain or a post-2009 strain.

4. The monoclonal antibody, or the antigen binding fragment thereof, according to claim 1, wherein the binding fragment is an Fab, an Fab', an $F(ab')_2$, or a scFv fragment.

5. A method for treating or preventing H1N1 infection, comprising administering to a subject in need thereof the antibody, or the antigen binding fragment thereof, according to claim 1.

6. The method according to claim 5, wherein the antibody comprises a heavy chain having the amino acid sequence of SEQ ID NO: 2 and a light chain having the amino acid sequence of SEQ ID NO: 4.

7. The method according to claim 5, wherein the H1N1 is a 2009 strain or a post-2009 strain.

8. The method according to claim 5, wherein the antigen binding fragment is an Fab, an Fab', an $F(ab')_2$, or a scFv fragment.

9. A method for detecting H1N1 virus, comprising:

contacting a test sample with the antibody, or the antigen binding fragment thereof, according to claim 1; and determining presence or absence of binding with the antibody, or the antigen binding fragment thereof, wherein presence of the binding indicates existence of H1N1virus in the test sample.

* * * * *

SEQUENCE LISTING

```
<160> NUMBER OF SEQ ID NOS: 10

<210> SEQ ID NO 1
<211> LENGTH: 1422
<212> TYPE: DNA
<213> ORGANISM: Homo spiens

<400> SEQUENCE: 1
atgaaacacc cgtggttctt cctcctcctg gtggcagctc ccagatgggt cctgtcccag      60
gtgcagctgc aggagtcggg cccaggactg gtgaagcctt cggagaccct gtccctcacc     120
tgcactgtct ctggtggctc cgtcaacact ggcagttact actggagctg gatccggcag     180
cccccaggga agggactgga gtggattgcg tattcctctg tcagtgggac ctccaactac     240
```

-continued

```
aatccctccc tcaagagtcg agtcaccctg acagtagaca cgtccaagaa ccagttctcc    300
ctgagcgtga ggtctgtgac cgctgcggac acggccgtat atttctgtgc gagactaaat    360
tacgatattt tgactggtta ttacttcttt gacttctggg gccagggaac cctggtcatc    420
gtctcctcag cctccaccaa gggcccatcg gtcttccccc tggcaccctc ctccaagagc    480
gcctctgggg gcacagcggc cctgggctgc ctggtcaagg actacttccc cgaaccggtg    540
acggtgtcgt ggaactcagg cgccctgacc agcggcgtgc acaccttccc ggctgtccta    600
cagtcctcag gactctactc cctcagcagc gtggtgaccg tgccctccag cagctcgggc    660
acccagacct acatctgcaa cgtgaatcac aagcccagca acaccaaggt ggacaagaga    720
gttgagccca atcttgtga caaaactcac acatgcccac cgtgcccagc acctgaactc    780
ctgggggggac cgtcagtctt cctcttcccc ccaaaaccca aggacaccct catgatctcc    840
cggacccctg aggtcacatg cgtggtggtg gacgtgagcc acgaagaccc tgaggtcaag    900
ttcaactggt acgtggacgg cgtggaggtg cataatgcca agacaaagcc gcgggaggag    960
cagtacaaca gcacgtaccg tgtggtcagc gtcctcaccg tcctgcacca ggactggctg   1020
aatggcaagg agtacaagtg caaggtctcc aacaaagccc tcccagcccc catcgagaaa   1080
accatctcca aagccaaagg gcagccccga gaaccacagg tgtacaccct gcccccatcc   1140
cgggatgagc tgaccaagaa ccaggtcagc ctgacctgcc tggtcaaagg cttctatccc   1200
agcgacatcg ccgtggagtg ggagagcaat gggcagccgg agaacaacta caagaccacg   1260
cctcccgtgc tggactccga cggctccttc ttcctctaca gcaagctcac cgtggacaag   1320
agcaggtggc agcaggggaa cgtcttctca tgctccgtga tgcatgaggc tctgcacaac   1380
cactacacgc agaagagcct ctccctgtct ccgggtaaat ga                       1422
```

<210> SEQ ID NO 2
<211> LENGTH: 473
<212> TYPE: PRT
<213> ORGANISM: Homo sapiens

<400> SEQUENCE: 2

```
Met Lys His Pro Trp Phe Phe Leu Leu Leu Val Ala Ala Pro Arg Trp
  1               5                  10                  15

Val Leu Ser Gln Val Gln Leu Gln Glu Ser Gly Pro Gly Leu Val Lys
             20                  25                  30

Pro Ser Glu Thr Leu Ser Leu Thr Cys Thr Val Ser Gly Gly Ser Val
         35                  40                  45

Asn Thr Gly Ser Tyr Tyr Trp Ser Trp Ile Arg Gln Pro Pro Gly Lys
     50                  55                  60

Gly Leu Glu Trp Ile Ala Tyr Ser Ser Val Ser Gly Thr Ser Asn Tyr
 65                  70                  75                  80

Asn Pro Ser Leu Lys Ser Arg Val Thr Leu Thr Val Asp Thr Ser Lys
                 85                  90                  95

Asn Gln Phe Ser Leu Ser Val Arg Ser Val Thr Ala Ala Asp Thr Ala
            100                 105                 110

Val Tyr Phe Cys Ala Arg Leu Asn Tyr Asp Ile Leu Thr Gly Tyr Tyr
        115                 120                 125

Phe Phe Asp Phe Trp Gly Gln Gly Thr Leu Val Ile Val Ser Ser Ala
    130                 135                 140

Ser Thr Lys Gly Pro Ser Val Phe Pro Leu Ala Pro Ser Ser Lys Ser
145                 150                 155                 160
```

```
Ala Ser Gly Gly Thr Ala Ala Leu Gly Cys Leu Val Lys Asp Tyr Phe
            165                 170                 175
Pro Glu Pro Val Thr Val Ser Trp Asn Ser Gly Ala Leu Thr Ser Gly
        180                 185                 190
Val His Thr Phe Pro Ala Val Leu Gln Ser Ser Gly Leu Tyr Ser Leu
    195                 200                 205
Ser Ser Val Val Thr Val Pro Ser Ser Ser Leu Gly Thr Gln Thr Tyr
210                 215                 220
Ile Cys Asn Val Asn His Lys Pro Ser Asn Thr Lys Val Asp Lys Arg
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Ala Leu His Asn His Tyr Thr Gln
    450                 455                 460
Lys Ser Leu Ser Leu Ser Pro Gly Lys
465                 470
```

<210> SEQ ID NO 3
<211> LENGTH: 711
<212> TYPE: DNA
<213> ORGANISM: Homo sapiens

<400> SEQUENCE: 3

```
atggcttgga cccactcct cttcctcacc ctcctcctcc actgcacagg gtctctctcc      60
caggttgagc tgactcaatc gccctctgcc tctgcctccc tgggaacctc ggtcaagctc    120
acctgcactt tgagtagtgg gcacagcacc tacgccatcg cgtggcatca gcagcggcca    180
gggaagggcc ccggtacct gatgaatctt agcagtggag cagacacac caggggggac    240 gggatcctg atcgcttctc gggctccagc tctggggctg accgctacct catcatctcc    300
agcctccagt ctgaggatga ggctgactat tactgtcaga cctgggacgc tggcatggta    360
```

```
ttcggcggag ggaccaagct gaccgtccta ggtcagccca aggctgcccc ctcggtcact      420
ctgttcccgc cctcctctga ggagcttcaa gccaacaagg ccacactggt gtgtctcata      480
agtgacttct acccgggagc cgtgacagtg gcctggaagg cagatagcag ccccgtcaag      540 gcggagtgg agaccaccac accctccaaa caaagcaaca caagtacgc ggccagcagc        600 tatctgagcc tgacgcctga gcagtggaag tcccacagaa gctacagctg ccaggtcacg      660
catgaaggga gcaccgtgga gaagacagtg gcccctacag aatgttcata g               711

<210> SEQ ID NO 4
<211> LENGTH: 236
<212> TYPE: PRT
<213> ORGANISM: Homo sapiens

<400> SEQUENCE: 4

Met Ala Trp Thr Pro Leu Leu Phe Leu Thr Leu Leu Leu His Cys Thr
1               5                   10                  15

Gly Ser Leu Ser Gln Val Glu Leu Thr Gln Ser Pro Ser Ala Ser Ala
            20                  25                  30

Ser Leu Gly Thr Ser Val Lys Leu Thr Cys Thr Leu Ser Ser Gly His
        35                  40                  45

Ser Thr Tyr Ala Ile Ala Trp His Gln Gln Arg Pro Gly Lys Gly Pro
    50                  55                  60

Arg Tyr Leu Met Asn Leu Ser Ser Gly Gly Arg His Thr Arg Gly Asp
65                  70                  75                  80

Gly Ile Pro Asp Arg Phe Ser Gly Ser Ser Ser Gly Ala Asp Arg Tyr
                85                  90                  95

Leu Ile Ile Ser Ser Leu Gln Ser Glu Asp Glu Ala Asp Tyr Tyr Cys
            100                 105                 110

Gln Thr Trp Asp Ala Gly Met Val Phe Gly Gly Thr Lys Leu Thr
        115                 120                 125

Val Leu Gly Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235

<210> SEQ ID NO 5
<211> LENGTH: 12
<212> TYPE: PRT
<213> ORGANISM: Homo sapiens

<400> SEQUENCE: 5

Gly Gly Ser Val Asn Thr Gly Ser Tyr Tyr Trp Ser
1               5                   10

<210> SEQ ID NO 6
```

```
<211> LENGTH: 9
<212> TYPE: PRT
<213> ORGANISM: Homo sapiens

<400> SEQUENCE: 6

Tyr Ser Ser Val Ser Gly Thr Ser Asn
1               5

<210> SEQ ID NO 7
<211> LENGTH: 14
<212> TYPE: PRT
<213> ORGANISM: Homo sapiens

<400> SEQUENCE: 7

Leu Asn Tyr Asp Ile Leu Thr Gly Tyr Tyr Phe Phe Asp Phe
1               5                   10

<210> SEQ ID NO 8
<211> LENGTH: 12
<212> TYPE: PRT
<213> ORGANISM: Homo sapiens

<400> SEQUENCE: 8

Thr Leu Ser Ser Gly His Ser Thr Tyr Ala Ile Ala
1               5                   10

<210> SEQ ID NO 9
<211> LENGTH: 7
<212> TYPE: PRT
<213> ORGANISM: Homo sapiens

<400> SEQUENCE: 9

Leu Met Asn Leu Ser Ser Gly
1               5

<210> SEQ ID NO 10
<211> LENGTH: 8
<212> TYPE: PRT
<213> ORGANISM: Homo sapiens

<400> SEQUENCE: 10

Gln Thr Trp Asp Ala Gly Met Val
1               5
```